(12) United States Patent
Masumura

(10) Patent No.: US 10,194,803 B2
(45) Date of Patent: Feb. 5, 2019

(54) CONTROL APPARATUS, MEASUREMENT APPARATUS, CONTROL METHOD, AND STORAGE MEDIUM

(71) Applicant: CANON KABUSHIKI KAISHA, Tokyo (JP)

(72) Inventor: Takahiro Masumura, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 264 days.

(21) Appl. No.: 15/152,759

(22) Filed: May 12, 2016

(65) Prior Publication Data

US 2016/0338592 A1    Nov. 24, 2016

(30) Foreign Application Priority Data

May 20, 2015   (JP) ................................ 2015-102449

(51) Int. Cl.
```
A61B 5/00      (2006.01)
A61B 5/02      (2006.01)
G01N 21/47     (2006.01)
G01N 21/49     (2006.01)
```

(52) U.S. Cl.
CPC ........ *A61B 5/0059* (2013.01); *A61B 5/02007* (2013.01); *G01N 21/4795* (2013.01); *A61B 2562/0233* (2013.01); *A61B 2576/00* (2013.01); *G01N 21/49* (2013.01); *G01N 2201/069* (2013.01)

(58) Field of Classification Search
CPC .............. A61B 5/0059; A61B 5/02007; A61B 2562/0233; A61B 2576/00; G01N 21/4795; G01N 21/49

USPC ......................................................... 600/479
See application file for complete search history.

(56) References Cited

U.S. PATENT DOCUMENTS

| | | | |
|---|---|---|---|
| 5,750,994 A | 5/1998 | Schlager | |
| 6,076,010 A | 6/2000 | Boas et al. | |
| 7,447,408 B2* | 11/2008 | Bouma | ............. G02B 6/02042 356/300 |
| 7,567,349 B2* | 7/2009 | Tearney | ............... A61B 5/0059 356/479 |

(Continued)

FOREIGN PATENT DOCUMENTS

| | | |
|---|---|---|
| JP | 9-159606 A | 6/1997 |
| JP | 2012223283 A | 11/2012 |

(Continued)

OTHER PUBLICATIONS

Extended European Search Report issued in European Appln. No. 16169532.5, dated Oct. 11, 2016.

(Continued)

*Primary Examiner* — Christopher A Flory
(74) *Attorney, Agent, or Firm* — Rossi, Kimms & McDowell LLP

(57) ABSTRACT

A control apparatus includes a data acquiring unit configured to acquire a measured signal obtained by measuring light emitted from a test object onto which light is irradiated, a processing unit configured to calculate an objective function that varies in accordance with a statistical value obtained by statistically processing the measured signal, and a controller configured to control a modulation amount of a wavefront of the light irradiated onto the test object so as to minimize the objective function.

12 Claims, 7 Drawing Sheets

(56) References Cited

U.S. PATENT DOCUMENTS

| | | | | |
|---|---|---|---|---|
| 7,761,139 | B2* | 7/2010 | Tearney | A61B 5/0066 600/473 |
| 8,509,879 | B2* | 8/2013 | Durkin | A61B 5/0073 600/407 |
| 8,817,255 | B2 | 8/2014 | Masumura | |
| 9,261,458 | B2 | 2/2016 | Tamano | |
| 2005/0226636 | A1* | 10/2005 | Hiramatsu | H01S 5/02228 398/182 |
| 2008/0002211 | A1* | 1/2008 | Park | G01N 21/4795 356/512 |
| 2008/0025570 | A1* | 1/2008 | Fingler | A61B 3/102 382/107 |
| 2008/0291463 | A1* | 11/2008 | Milner | A61B 1/00096 356/491 |
| 2009/0118622 | A1 | 5/2009 | Durkin et al. | |
| 2009/0245077 | A1* | 10/2009 | Ueda | G11B 7/00451 369/121 |
| 2010/0069750 | A1* | 3/2010 | Masumura | A61B 5/0059 600/437 |
| 2011/0083509 | A1 | 4/2011 | Li et al. | |
| 2012/0095354 | A1* | 4/2012 | Dunn | A61B 5/0261 600/504 |
| 2012/0127557 | A1 | 5/2012 | Masumura | |
| 2012/0130253 | A1* | 5/2012 | Nadkarni | A61B 5/0059 600/476 |
| 2013/0109963 | A1* | 5/2013 | Zhu | A61B 8/0825 600/427 |
| 2013/0182253 | A1 | 7/2013 | Cui | |
| 2013/0296701 | A1* | 11/2013 | Zalev | A61B 5/0095 600/440 |
| 2014/0046165 | A1 | 2/2014 | Fukutani | |
| 2014/0073917 | A1* | 3/2014 | Huang | A61B 5/0066 600/427 |
| 2014/0206980 | A1 | 7/2014 | Lee et al. | |
| 2014/0378845 | A1* | 12/2014 | Nadkarni | A61B 5/0084 600/478 |
| 2016/0220129 | A1* | 8/2016 | Ostroverkhov | A61B 5/0261 |
| 2016/0232427 | A1* | 8/2016 | Huang | G01N 33/4833 |
| 2016/0278715 | A1* | 9/2016 | Yu | A61B 5/7275 |

FOREIGN PATENT DOCUMENTS

| | | |
|---|---|---|
| JP | 2015018045 A | 1/2015 |
| WO | 2012080838 A2 | 6/2012 |
| WO | 2015031395 A1 | 3/2015 |

OTHER PUBLICATIONS

Donkey et al. "Genetic algorithm optimization for focusing through turbid media in noisy environments." Optics Express. Feb. 27, 2012:4840-4849. vol. 20, No. 5.

Ma et al. "Time-reversed adapted-perturbation (TRAP) optical focusing onto dynamic objects inside scattering media." Mature Photonics. Nov. 2, 2014:931-936. vol. 8, No. 12.

Vellekoop et al. "Demixing light paths inside disordered metamaterials." Optics Express. Jan. 7, 2008:67-80. vol. 16, No. 1.

Liu et al. "Motion-contrast speckle imaging of microcirculation within tissue beds in vivo." Journal of Biomedical Optics. Jun. 2013:060508-1-060508-3. vol. 18, No. 6.

Vellekoop et al. "Focusing Coherent Light Through Opaque Strongly Scattering Media," Optics Letters. Aug. 15, 2007.vol. 32, No. 16 2309-2311.

Ma et al. "Time-Reversed Adapted-Perturbation (TRAP) Optical Focusing Onto Dynamic Objects Inside Scattering Media," Nature Photonics. Published online Nov. 2, 2014. 6.

Donkey et al. "Genetic Algorithm Optimization for Focusing Through Turbid Media in Noisy Environments," Optics Express. vol. 20, No. 5. Feb. 27, 2012.4840-4849.

Caravaca-Aguirre et al. "Real-Time Resilient Focusing Through a Bending Multimode Fiber," Optics Express. vol. 21, No. 10. May 20, 2013. 12881-12887.

Liu et al. "Motion-Contrast Laser Speckle Imaging of Microcirculation Within Tissue Beds In Vivo," Journal of Biomedical Optics. vol. 8(6). Jun. 2013. 060508-1-060508-3.

* cited by examiner

CONTROL APPARATUS, MEASUREMENT APPARATUS, CONTROL METHOD, AND STORAGE MEDIUM

BACKGROUND OF THE INVENTION

Field of the Invention

The present invention relates generally to a control apparatus, and more particularly to a control apparatus configured to control measuring of an optical property in a test object.

Description of the Related Art

I. M. Vellekoop and A. P. Mosk, "Focusing coherent light through opaque strongly scattering media," Optics Letters Vol. 32, No. 16 2309-2311 (2007) (simply referred to as "Vellekoop" hereinafter) discloses a technology for irradiating light onto a scattering medium as a test object, such as biological tissues, and for observing scattered light with a CCD which has transmitted through the medium. Vellekoop also discloses a technology for shaping an incident wavefront using a spatial light modulator ("SLM") so as to improve a light intensity at a specific position in a captured image. Vellekoop demonstrates that the light can be focused on an arbitrary position through the medium after iteration process of measuring the transmitted light intensity and of shaping the incident wavefront. By applying this technology, U.S. Patent Application Publication No. 2013/0182253 discloses a technology using a fluorescent (such as a multiphoton absorption) signal, as a monitoring signal, instead of the transmitted light intensity. U.S. Patent Application Publication No. 2013/0182253 shapes an incident wavefront so as to improve the fluorescent signal, focuses the light on a fluorescent light emitting spot in a medium, and images the fluorescent signal. The technologies of U.S. Patent Applications Publication Nos. 2011/0083509 and 2012/0127557 utilize a focused ultrasound: U.S. Patent Application Publication No. 2011/0083509 uses a photoacoustic signal as a monitoring signal, and U.S. Patent Application Publication No. 2012/0127557 uses ultrasound modulated and frequency-shifted light (ultrasound modulated light) as the monitoring signal. U.S. Patent Applications Publication Nos. 2011/0083509 and 2012/0127557 can focus the light on an ultrasound focus position in the medium by shaping the incident wavefront so as to improve the monitoring signal. Thus, the light can be focused on a position by a distance longer than a transport mean free path inside or through the medium by combining the monitoring signal with the wavefront shaping. U.S. Patent Applications Publication Nos. 2011/0083509 and 2012/0127557 can image inside the medium utilizing the monitoring signal with a high signal-to-noise ratio ("SNR") by improving the intensity of the monitoring signal. C. Ma et al., "Time-reversed adapted-perturbation (TRAP) optical focusing onto dynamic objects inside scattering media," Nature Photonics, (2014) (simply referred to as "Ma" hereinafter) discloses a technology for focusing light in the medium utilizing displacement of a scatterer or a change of light absorption property in the medium without using a fluorescent probe or a focused ultrasound. Ma records two scattered waves in holograms before and after those intrinsic changes of the medium, and generates a phase conjugate wave based on a wavefront obtained from a difference between these two scattered wavefronts, and again illuminates the medium with the phase conjugate wave. It is demonstrated that the phase conjugate wave propagates to a local position at which the intrinsic change occurs and the inside of the medium can be imaged by utilizing this effect.

In order to focus light in the scattering medium (the test object) utilizing the above wavefront shaping technology, it is necessary to monitor a signal generated from the local position in the test object. When a fluorescent probe is used as the monitoring signal as in U.S. Patent Application Publication No. 2013/0182253, it is necessary to inject the fluorescent probe into the test object and this injection is invasive to the test object. After the injection, it is difficult to arbitrarily change the position of the fluorescent probe, and therefore the light focus position is limited. When the ultrasound is used as in U.S. Patent Applications Publication Nos. 2011/0083509 and 2012/0127557, a ultrasound focus position as well as focus size can be freely controlled from the outside of the test object. However, the apparatus needs an ultrasound system including ultrasound probe, and the ultrasound probe needs to be contacted with the test object and also a matching solution (layer) is necessary between the ultrasound probe and the test object so as to introduce the ultrasound into the test object (acoustic matching). Therefore, in measuring the test object in a noninvasive and noncontact manner, the fluorescence or ultrasound cannot be used as the monitoring signal. On the other hand, a method for utilizing a change of an endogenous optical property in the medium, as in Ma, enables light to be focused in the test object in a noninvasive and noncontact manner and to form an image. Nevertheless, this method which needs generation of the phase conjugate wave, requires the scattered wave emitted from the test object to be recorded in the hologram, where a reference optical path is separately required for the interference measurement. In particular, a transmission type arrangement needs to place detectors in such a manner that the detector can detect object light and reproduced light at both sides of the test object, where object light and reproduced light are passing through the test object in recording and replaying the hologram respectively. As a result, the measurement apparatus becomes relatively complicated. In addition, when an unexpected noise is applied to the endogenous signal before and after the optical property changes, the phase conjugate wave obtained by the difference cannot be correctly focused on the changing spot.

SUMMARY OF THE INVENTION

The present invention provides a control apparatus, a measurement apparatus, a control method, and a storage medium advantageous to a measurement of an optical property in a test object.

A control apparatus according to one aspect of the present invention includes a data acquiring unit configured to acquire a measured signal obtained by measuring light emitted from a test object onto which light is irradiated, a processing unit configured to calculate an objective function that varies in accordance with a statistical value obtained by statistically processing the measured signal, and a controller configured to control a modulation amount of a wavefront of the light irradiated onto the test object so as to minimize the objective function.

Further features of the present invention will become apparent from the following description of exemplary embodiments with reference to the attached drawings.

DESCRIPTION OF THE EMBODIMENTS

It has recently been studied to measure or image an optical property in a medium, such as biological tissues, in a noninvasive way or a less-invasive way using light ranging from visible to near infrared light. In general, light is randomly scattered when it is propagating in a biological tissue and thus does not go straight beyond the transport mean free path $l_t'$. Therefore, light cannot be focused on a position deeper than the transport mean free path $l_t'$, which is about 1 mm in biological tissue. This fundamental problem causes a deteriorated resolution and a reduced measurement depth (penetration depth) in biological optical imaging. There is a conventional imaging method such as confocal microscopy or OCT (Optical Coherence Tomography) for example, which removes scattered light and extracts only signal light (non-scattered light or weakly scattered light having the very small number of scatterings). These methods typically have high resolutions, however, the penetration depth is less than 1 mm. In the depth deeper than the transport mean free path, the signal light exponentially decreases due to scattering.

As a solution for this fundamental scattering problem, the present invention adopts a technology that properly shapes a wavefront of light entering the above medium and efficiently sends light to a specific position in the scattering medium.

A description will now be given of embodiments according to the present invention with reference to the accompanying drawings.

Figure 1:
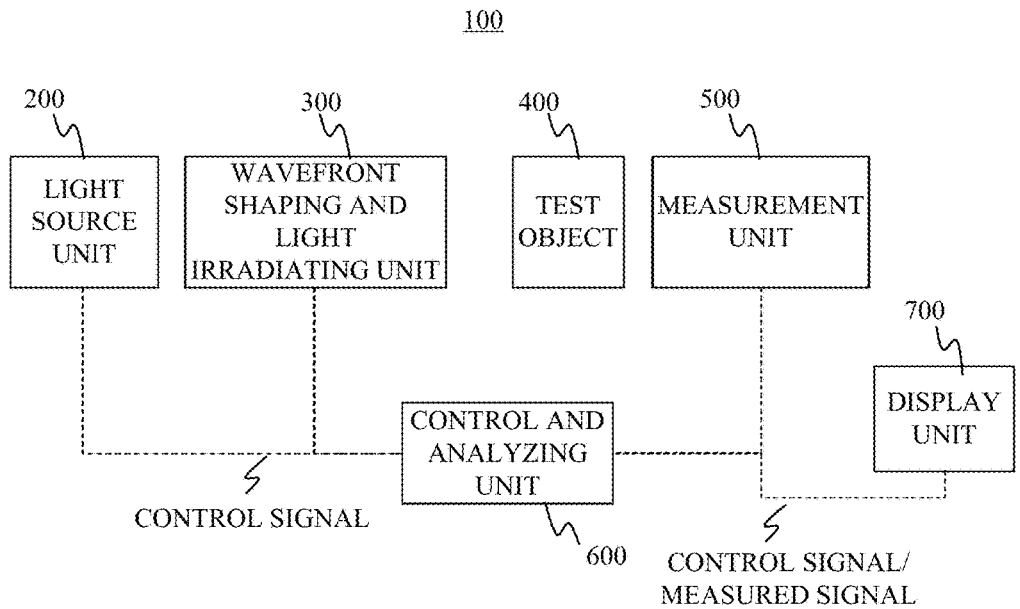
FIG. 1 is a schematic diagram illustrating an imaging apparatus (measurement apparatus) according to one embodiment of the present invention.

FIG. 1 schematically illustrates a basic configuration of an imaging apparatus (measurement apparatus) according to the present invention. The imaging apparatus 100 includes a light source unit 200, a wavefront shaping and light irradiating unit 300, a measurement unit 500, a control and analyzing unit 600, and a display unit 700. The test object 400 to be measured including a living tissue, and its optical property, such as scattering property or absorption property, changes with time at a certain local position in the test object. In other words, the test object 400 contains an area in which the optical property, such as the scattering property or the absorption property, changes with time.

Figure 2:
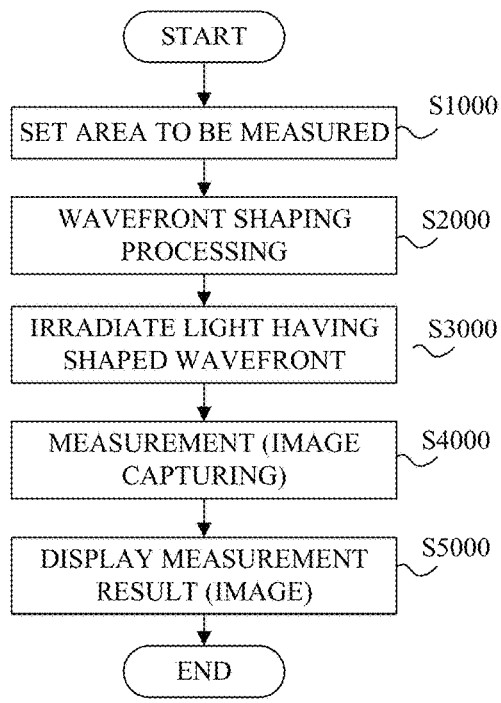
FIG. 2 is a schematic view of a measuring and imaging process flow according to this embodiment of the present invention.

The light source unit 200 includes a light source configured to emit light ranging from visible to near infrared wavelength, the wavefront of the light emitted from the light source is shaped by the wavefront shaping and light irradiating unit 300. The wavefront-shaped light enters the test object 400. The measurement unit 500 measures the light emitted from the test object, such as transmitted light or reflected light. The control and analyzing unit 600 controls each component in accordance with processing flow illustrated in FIG. 2. Thus, the control and analyzing unit 600 serves as a control apparatus that controls the light source unit 200, the wavefront shaping and light irradiating unit 300, the measurement unit 500, and the display unit 700. The control and analyzing unit 600 also analyzes a signal measured by the measurement unit 500. A measurement result analyzed by the control and analyzing unit 600 is output to the display unit 700. FIG. 2 is a view illustrating a basic processing flow of the imaging method according to the present invention. Each step in the flowchart in FIG. 2 is executed by a command of a CPU in the control and analyzing unit 600. At first, in S1000, the CPU sets an area to be measured (measurement area) in the test object 400. The wavefront shaping and light irradiating unit 300 and the measurement unit 500 are controlled in such a way that the light can be irradiated onto the area, and the transmitted or reflected light from the test object 400 is measured. Next, in S2000, the wavefront of the light entering the test object 400 is shaped by wavefront shaping process which will be described later. Next, in S3000, the wavefront-shaped light is irradiated onto the test object. Next, in S4000, the light emitted from the test object is measured (captured) using the measurement unit 500. The CPU performs necessary processing for the obtained measurement data or captured image through the control and analyzing unit 600, and then displays the measurement result (image) on the display unit 700 in S5000. The basic apparatus and processing according to the present invention have thus discussed, and a variety of embodiments will be described below.

First Embodiment

Figure 3:
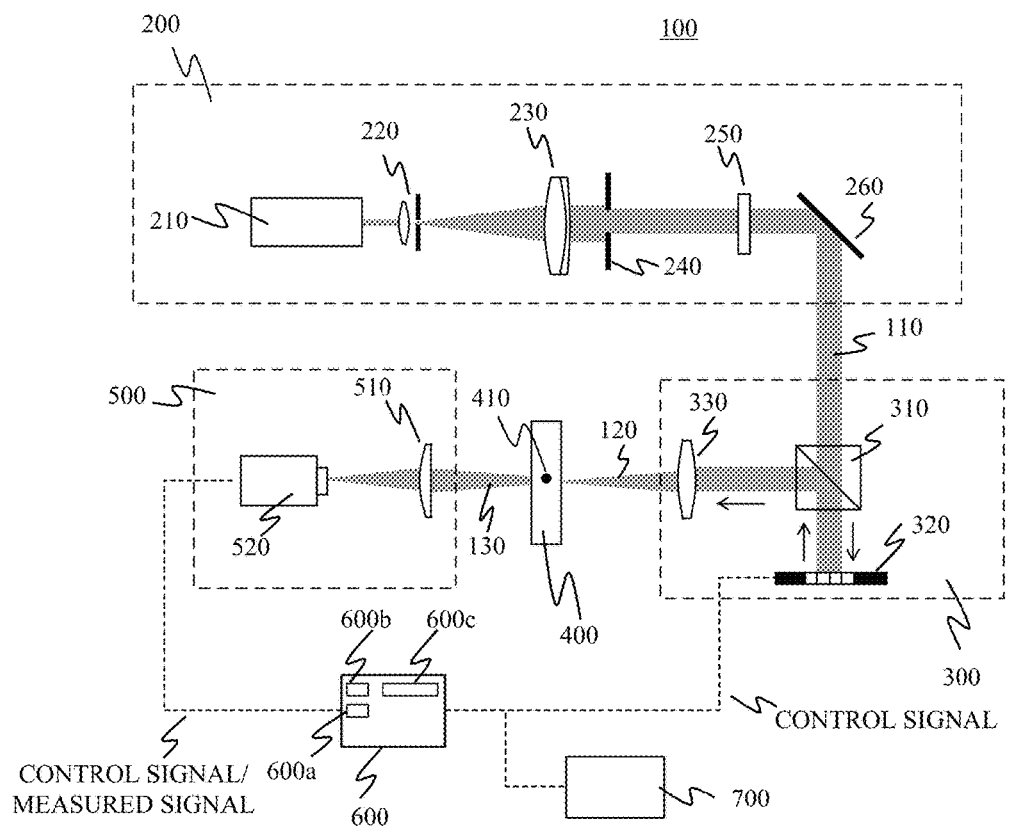
FIG. 3 is a schematic view of an apparatus according to a first embodiment.

A description will now be given of an imaging apparatus and an imaging method according to a first embodiment of the present invention. Those elements, which are corresponding elements in FIGS. 1 and 2, will be designated by the same reference numerals, and a description thereof will be omitted. FIG. 3 is a view of an illustrative apparatus according to this embodiment. The imaging apparatus according to this embodiment sets a living tissue, such as a finger or a hand, as the test object 400, captures an image of blood vessel 410 in the test object 400, and provides the image used for medical applications, such as diagnosis.

The light source unit 200 includes a light source 210, and outputs light 110 collimated with a predetermined beam size by the light source unit 200. In an example, the light source 210 is a laser that emits continuous wave ("CW") light having a constant intensity with time in a range from visible wavelength to near infrared wavelength, such as 400 nm to 1,500 nm. For example, the wavelength may correspond to an absorption spectrum, such as water, fat, protein, oxy-hemoglobin, deoxy-hemoglobin as a main ingredient of the test object 400. Alternatively, the wavelength may be outside of the above range if necessary, and the laser may emit light having an intensity modulated at an arbitrary frequency or pulsed light. The light intensity irradiated onto the test object 400 is adjusted so as to satisfy the safety standard. The light emitted from the light source 210 has a sufficiently long coherence length, such as several tens of centimeters or longer. The light emitted from the light source 210 is collimated by a spatial filter 220 and a lens 230, and the beam size and the light intensity are properly adjusted by a variable aperture diaphragm 240 and an ND filter 250. The light intensity can be adjusted by directly adjusting the output of the light source 210 instead of the ND filter 250. The beam size is adjusted based on the effective region of a spatial light modulator 320, which will be described later.

The light 110 having the adjusted beam size and light intensity is reflected by the mirror 260, is output from the light source unit 200, and enters the wavefront shaping and light irradiating unit 300. The input light 110 transmits a beam splitter ("BS") 310 and enters a spatial light modulator ("SLM") 320. The SLM 320 can use, for example, a liquid crystal on silicon ("LCOS"). The SLM 320 may be a reflection type device, or a transmission type device. The SLM 320 is connected to the control and analyzing unit 600 such as PC, and shapes (phase-modulates) the wavefront based on the processing of the wavefront shaping process S2000 in FIG. 2. In other words, the SLM 320 serves as a modulator configured to modulate the wavefront of the light entering the test object 400. The polarization of the light entering the SLM 320 is adjusted so as to correspond to a polarization direction in which the phase modulation of the SLM 320 works. The wavefront-shaped light 120 reflected on the SLM 320 is reflected on the BS 310, passes through the lens (optical system) 330, and is output from the wavefront shaping and light irradiating unit 300. The light output from the wavefront shaping and light irradiating unit 300 enters and illuminates the test object 400. Each of a distance between the lens 330 and the SLM 320 and a distance between the lens 330 and the incident surface of the test object 400 is equal to a focal length of the lens 330. The SLM 320 and the incident surface of the test object 400 have a Fourier transform relationship, and a Fourier-transformed distribution of the wavefront-shaped light by the SLM 320 enters the test object 400.

Scattered light 130 emitted from the test object 400 enters the measurement unit 500 and is measured and an image is captured there. Thus, the measurement unit 500 serves to measure light emitted from the test object 400. The measurement unit 500 includes a lens (optical system) 510 and a CCD 520, and the scattered light 130 forms an image on the CCD 520 via the lens 510. As an area sensor, instead of the CCD, a CMOS sensor, an area sensor having an image intensifier, an EMCCD, a sCMOS are applicable. The CCD 520 is connected to and controlled by the PC 600. The image captured by the CCD 520 is sent to the PC 600, and received by a data acquiring unit 600a in the PC 600. The captured image obtained by the data acquiring unit 600a is analyzed by a processing unit 600b in the PC 600. The data acquiring unit 600a and the processing unit 600b are controlled by a control unit 600c in the PC 600. The analyzed and generated image is displayed on the monitor 700 as a display unit. In displaying an image on the monitor, image processing, such as edge emphasis, gamma correction, and color correction, may be performed so that the user can correctly recognize the measurement data and image, if necessary.

The test object 410 includes a blood vessel 410 to be measured in this apparatus, and a purpose of this embodiment is to enhance the visibility of the blood vessel 410 by sending light to or by focusing light onto the local position. For this purpose, this embodiment utilizes a temporal change of the optical property of the blood vessel 410 in the test object 400. Because of the blood flows in the blood vessel 410, a variety of micro objects (scatterers) such as cells flowing in the blood vessel move, which optically result in the change of the scattering property with time. The signal measured by the measurement unit 500 changes due to the influence of this change. If it is assumed that the optical property in an area other than the blood vessel 410 does not change in a certain measurement time period, a change of the signal contained in the measured signal is caused by the change of the optical property in the local blood vessel site. One characteristic of this embodiment is to extract this change by statistically processing the measured signal and to use the change as a monitoring signal in the wavefront shaping. Thereby, light can be efficiently focused on the local area (blood vessel volume) in the test object in a noninvasive and noncontact manner so as to form an image of the area without using the fluorescent probe or the ultrasound system.

Figure 4:
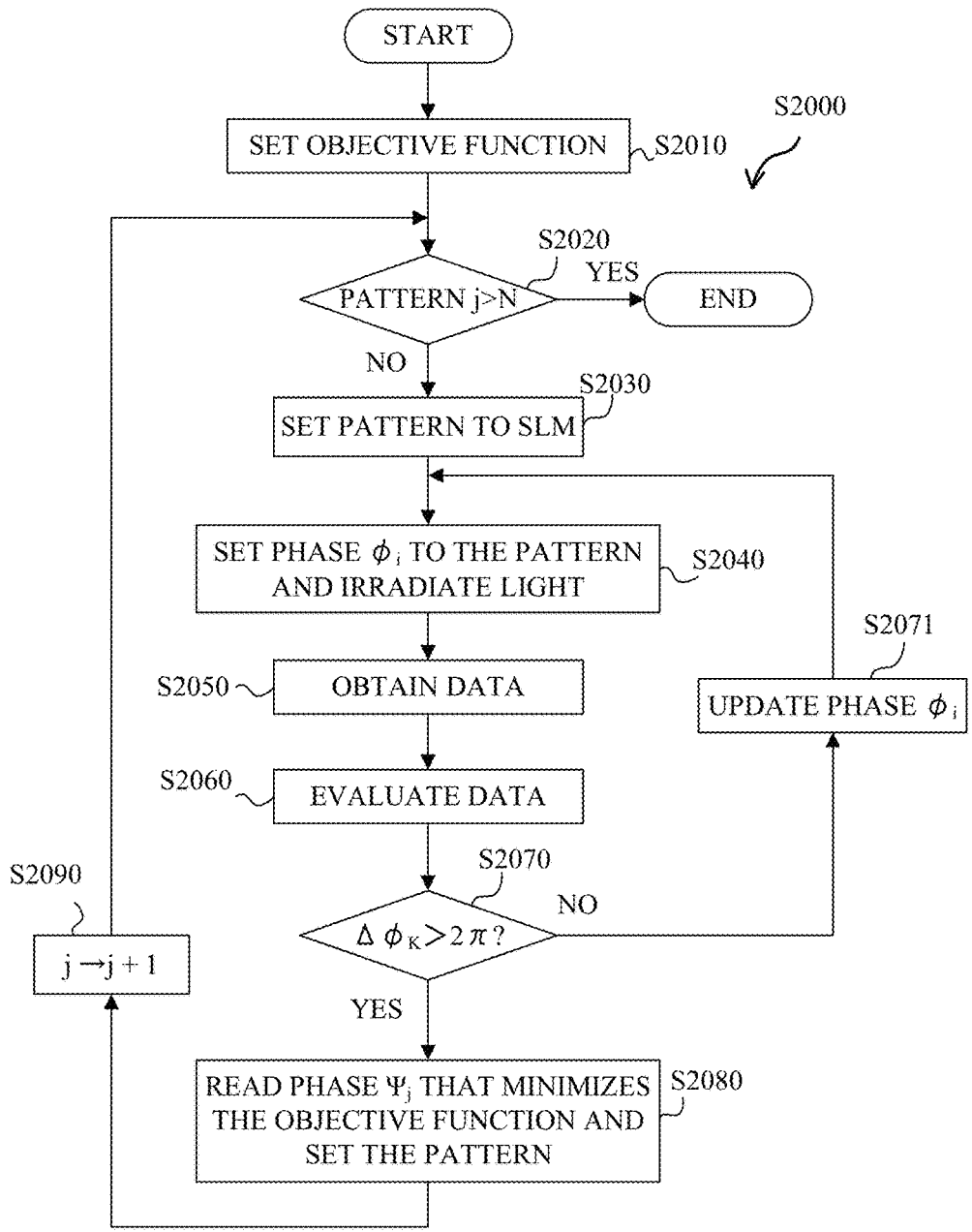
FIG. 4 is an illustrative wavefront shaping process flow according to the first embodiment.

A description of a processing flow of this embodiment including the wavefront shaping process utilizing above statistical processing will now be given. The basic flow is similar to the one illustrated in FIG. 2. As for setting the measurement area in S1000, the blood vessel 410 is set and, the wavefront shaping and light irradiating unit 300 and the measurement unit 500 are controlled so that the blood vessel 410 can be measured. Here, the measurement area may be set based on a previously captured image of the test object 400 in the pre-measurement. Referring now to FIG. 4, a description will be given of the wavefront shaping process in S2000. Each step in the flowchart in FIG. 4 is executed in accordance with a command by the controller 600c in the PC 600. First, an objective function is set in S2010 for wavefront shaping (optimizing). This objective function is based on a value obtained through the statistical processing (a statistical value) of the image captured by the CCD 520. More specifically, the speckle contrast $C_s$ expressed in Expression (1) calculated with the captured image is set as the objective function.

$$C_s = \sigma_s / \langle I \rangle \qquad (1)$$

where I is a light intensity measured at each pixel in the CCD, $\langle \rangle$ is an average value and $\sigma_s$ is a standard deviation of the light intensity I in the image.

Figure 5:
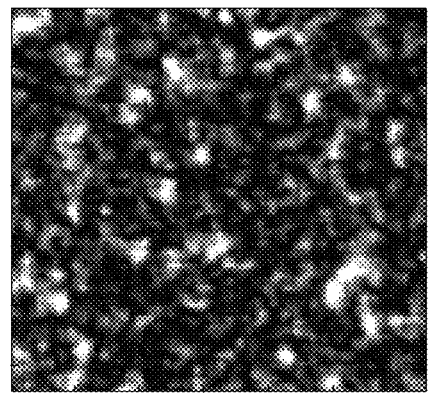
FIG. 5 is a schematic view of part of a measured signal according to the first embodiment.

The measurement unit 500 can acquire a temporal change of the optical property in the test object through a plurality of spatial measurements. The objective function is the speckle contrast that relies on the standard deviation of the light intensity I and the average value as expressed in Expression (1). Since the incident light 120 has a relatively long coherence length, the image captured by the CCD 520 is an image 800 containing a random speckle pattern, as schematically illustrated in FIG. 5. The measurement unit 500 is controlled so as to properly adjust the speckle grain size, in order to resolve the speckle grain by the CCD 520, and to measure the speckle contrast $C_s$. At the same time, the speckle grain size may be maintained as small as possible so as to measure as many speckle grains as possible, and evaluate the speckle contrast $C_s$ with a statistically large number. Therefore, the pixel size of the CCD 520 may be equal to the speckle grain size or the speckle grain size may slightly be larger than the pixel size of the CCD 520 by several pixels. Here, the fluctuation range of the speckle contrast $C_s$ in the imaging apparatus 100 may be previously measured and set as a system noise to be used in the following process.

Figure 6A:
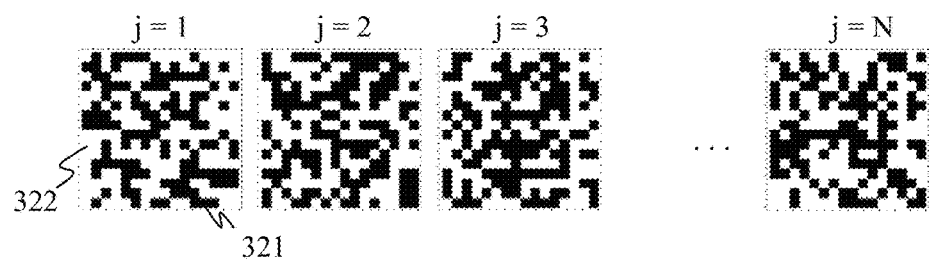
FIGS. 6A to 6C are schematic views of patterns used for the wavefront shaping process according to the first embodiment.
Figure 6B:
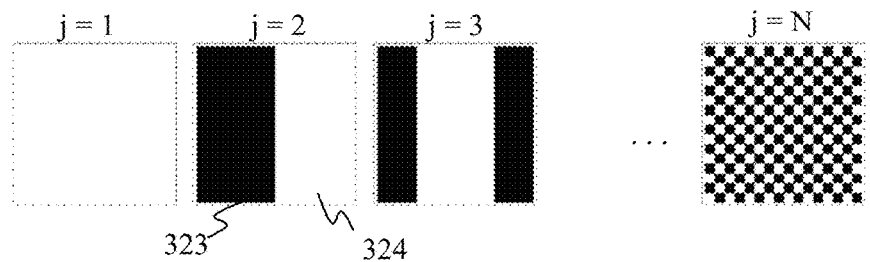
Figure 6C:
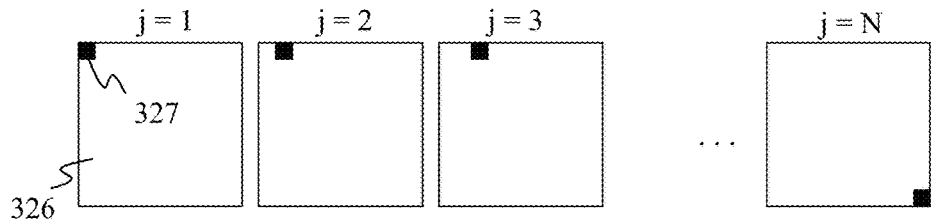

Next, in S2020, the j-th phase modulation pattern (j=1 to N) to be loaded into the SLM 320 is selected. In the following process from S2030 to S2080, the wavefront of the light incident on the test object 400 will be modulated (or shaped) by this pattern. FIGS. 6A to 6C illustrate some patterns. For example, a randomly distributed pattern of a modulated area 321 (illustrated in black) and a non-modulated area 322 (illustrated in white) may be used, as illustrated in FIG. 6A. Alternatively, Hadamard basis illustrated in FIG. 6B may be used to set a modulated area 323 and a non-modulated area 324, or areas 323 and 324 are set as the modulated areas with π phase difference in each other. Alternatively, as illustrated in FIG. 6C, one (single) segment 327 in the SLM 320 may be set as a pattern as the modulated area. In this case, the segment means an integrated area of a plurality of pixels in the SLM 320, and is a minimum unit for the phase modulation where the phase is uniformly modulated. The segment size may be arbitrarily set according to a measurement condition, and even the pixel size of the SLM can be set as the segment. Furthermore, an area 326 other than the segment 327 is the non-modulated area.

The number of patterns N may arbitrarily be set. As the number of patterns N increases, the SNR of the measured signal improves due to the focusing effect of the wavefront shaping. However, the large the number N, the more iterations required in S2020 and the longer the measurement time becomes. Therefore, the number of patterns N may be set by considering the balance between the measured signal SNR and the measurement time. In addition, each pattern may have a mutually orthogonal basis. After the j-th pattern is selected in S2020, the SLM 320 reads (sets) the pattern in S2030. Here, the pattern may be calculated and generated in S2020 on the fly, or the SLM 320 may read previously stored data out of the memory in the PC 600.

Next, in S2040, SLM 320 modulates the phase using the j-th pattern. The phase $\Phi_i$ of each pixel i (or segment j) in the j-th pattern is set onto the SLM 320 so as to shape the wavefront of the incident light 120, and to illuminate the test object 400. The phase of each pixel i is set as the phase distribution obtained in the (j−1)-th process. In S2050, the measurement unit 500 measures the light 130 emitted from the object 400. The data acquiring unit 600a obtains a captured image (measured signal) output from the measurement unit 500. Thus, the data acquiring unit 600a acquires a measured signal obtained by measuring light emitted from the test object. Next, in the evaluation of the measured data in S2060, the processing unit 600b calculates the objective function that varies according to the statistical value obtained by statistical processing of the acquired image. In other words, the processing unit 600b calculates the speckle contrast $C_s$ from the acquired image using Expression (1). The calculated speckle contrast $C_s$ is stored in the memory in the PC 600 with the value of the phase $\Delta\Phi_k$, which will be described later. In S2070, if the phase $\Delta\Phi_k$ exceeds 2π, the flow moves to S2080, and otherwise the flow moves to S2071, in which the controller 600c updates (changes) the value of the phase $\Phi_i$. Herein, the phase $\Delta\Phi_k$ is an update amount of the phase and determined by $\Delta\Phi_k = k \times \Delta\Phi$ (k=1 to $N_k$) with a discretized phase step size $\Delta\Phi$, where k is the iteration number in S2070, and $N_k$ is the number of discretization of phase. S2071 updates the phase $\Phi_i$ of the pixel i as $\Phi_i + \Delta\Phi_k$ ($\Phi_i \rightarrow \Phi_i + \Delta\Phi_k$). That is, the controller 600c controls a modulation amount of the wavefront of the light illuminating the test object 400. The step size $\Delta\Phi$ is set by considering the measurement accuracy and speed. In S2040 to S2060, similar to the above, the speckle contrast $C_s$ is calculated with the pattern of which phase is newly updated, and stored in the memory in the PC 600. This process is repeated until $\Delta\Phi_k$ exceeds 2π, and then the flow moves to S2080. In other words, until the flow moves to S2080, the controller 600c repeats the acquisition (S2050) by the data acquiring unit 600a and the calculation (S2060) by the processing unit 600b. In S2080, the measurement data relating to the phase modulation of the j-th pattern stored in the memory, the phase $\psi_j$ at which the speckle contrast $C_s$ (objective function) becomes minimum is loaded, and set to corresponding pixel i of the j-th pattern ($\Phi_i \rightarrow \Phi_i + \psi_j$). Thus, the controller 600c controls a modulation amount of a wavefront of the light illuminating the test object so as to minimize the objective function. More specifically, the controller 600c makes the data acquiring unit 600a and the processing unit 600b repeat the above process while changing the modulation amount, and determines the modulation amount where the objective function falls minimum. The controller 600c provides such control that the wavefront of the incident light is modulated with the phase distribution where the objective function is minimum. Next, in S2090, the flow moves to a next pattern (j+1) and the process of S2020 to S2080 will be repeated. The flow ends when all patterns are processed in S2020 (j=N). The above explained flow is the wavefront shaping process according to this embodiment, where the incident wavefront is shaped in such a manner that the speckle contrast $C_s$ (objective function) of the captured image becomes minimum.

The wavefront shaping process S2000 may use an algorithm that sequentially optimizes a phase of the pattern displayed in the SLM, as described above. Alternatively, a genetic algorithm as disclosed in Donald B. Conkey et al., "Genetic algorithm optimization for focusing through turbid media in noisy environments," Optics Express Vol. 20, No. 5 4840-4849 (2012) may be used. Thus, the wavefront shaping algorithm is not limited to the aforementioned algorithm but may use an arbitrary optimal algorithm. This embedment is characteristic in terms of setting the objective function as the speckle contrast calculated from the captured image. Furthermore, after the phase that minimizes the objective function is measured for all patterns, those phases may be set onto the SLM 320 simultaneously instead of setting one-by-one.

A description will now be given of the reason why the speckle contrast is set as the objective function. When the scattering property in the test object 400 does not change, for example, when there is no blood vessel 410, the speckle contrast $C_s$ does not change. On the other hand, when the light passes through the blood vessel 410 in the test object 400, because of the displacement of the scatterers caused by the blood flow, the scattering properties, such as a scatting direction and a transport mean free path, changes with time. As a result, the scattered light traces different paths (with a different optical path length) in the test object, and is emitted from the test object 400. When the measurement unit 500 measures the emitted light, a variety of scattered waves with random phases are incoherently superimposed, averaged and imaged in an exposure time period of the CCD 520. As a consequence, the speckle contrast $C_s$ of the image becomes smaller. Therefore, a change of the speckle contrast $C_s$ depends on a change of the changing site (blood vessel 410) as well as an amount of light passing through the changing site after the light enters the test object 400. The speckle contrast $C_s$ decreases as the light passing through the blood vessel 410 increases. Utilizing this effect, this embodiment sets the speckle contrast $C_s$ as an objective function. And the wavefront of the incident light is shaped so that the objective function becomes as small as possible. The incident wavefront obtained by this optimization generates a wavefront that is most influenced by the blood vessel 410. Therefore, irradiating this wavefront-shaped light results in the intensive irradiation onto the blood vessel 410 in the test object 400. As long as the change of the speckle image is evaluated as described above, the objective function is not limited to the speckle contrast $C_s$ and may use another statistical value, such as a variance $\sigma_s^2$ or a standard deviation $\sigma_s$ of the image. Thus, the statistical value according to this embodiment may be at least one of the standard deviation, the variance, and the average of the intensity of the captured image (measured signal).

After the wavefront shaping process in S2000 is completed, the wavefront-shaped light is irradiated onto the test object 400 and the blood vessel 410 in the test object is measured in the S3000 to S4000 in the measurement flow illustrated in FIG. 2. Thereby, the blood vessel 410 in the test object can be imaged with high contrast and high SNR, while it has conventionally been measured with low contrast and low SNR. The captured image may be displayed on the monitor 700. The captured image may be displayed in addition to another image, such as another diagnosis result or measurement data, which may be superimposed, if necessary.

The SLM 320 is not limited to the phase modulation SLM, but an amplitude modulation SLM may also be applicable. For example, the SLM may be a LCOS that modulates an amplitude or a digital mirror device ("DMD"). The DMD may generate a distribution of binary amplitude modulation by turning off the pixels in the DMD where the speckle contrast $C_s$ (the objective function) increases and by turning on the pixels where the objective function decreases. The test object may be measured with incident light shaped by this binary amplitude modulation. Alternatively, the phase may be modulated with a DMD of the binary amplitude modulation, as disclosed in Antonio M. Caravaca-Aguirre, Eyal Niv, Donald B. Conkey and Rafael Piestun et al., "Real-time resilient focusing through a bending multi-mode fiber," Optics Express Vol. 21, No. 10 12881-12887 (2012). It is desirable to use SLM which respond as fast as possible. Therefore, it is desirable to use DMD, which typically has a faster response speed than that of LCOS. Thus, the modulator configured to modulate the wavefront of the light irradiated onto the test object 400 may use at least one of the phase modulation or the amplitude modulation. Accordingly the controller 600c controls at least one of the phase modulation amount or the amplitude modulation amount.

The wavelength property (spectrum property) of the blood vessel 410 of the test object 400 may be visualized by repeating the measurement with a different wavelength of the light source 210. The above process with a plurality of arbitrary wavelengths can provide information regarding component ratio of oxy-hemoglobin, deoxy-hemoglobin, water, or metabolic information of oxygen saturation based on the spectral property of a measured blood vessel site.

Second Embodiment

A description will now be given of an imaging method and an imaging apparatus according to a second embodiment of the present invention. The configuration of the imaging apparatus according to this embodiment is the same as that of the first embodiment illustrated in FIG. 3, except the CCD 520 in the measurement unit 500, which is a CCD that can take images at high frame rate, such as several hundreds of frames per second ("fps") or higher. The measurement flow is similar to that of illustrated in FIG. 2, and the flow of the wavefront shaping process S2000 is basically similar to that in FIG. 4. This embodiment is different from the first embodiment as to setting the objective function in S2010, acquiring data in S2050, and evaluating the data in S2060. In S1000 or S2010, the controller 600c sets a target area in the captured image (measured signal). Here, the target area is an area in the test object 400 where the optical property changes with time.

Figure 7:
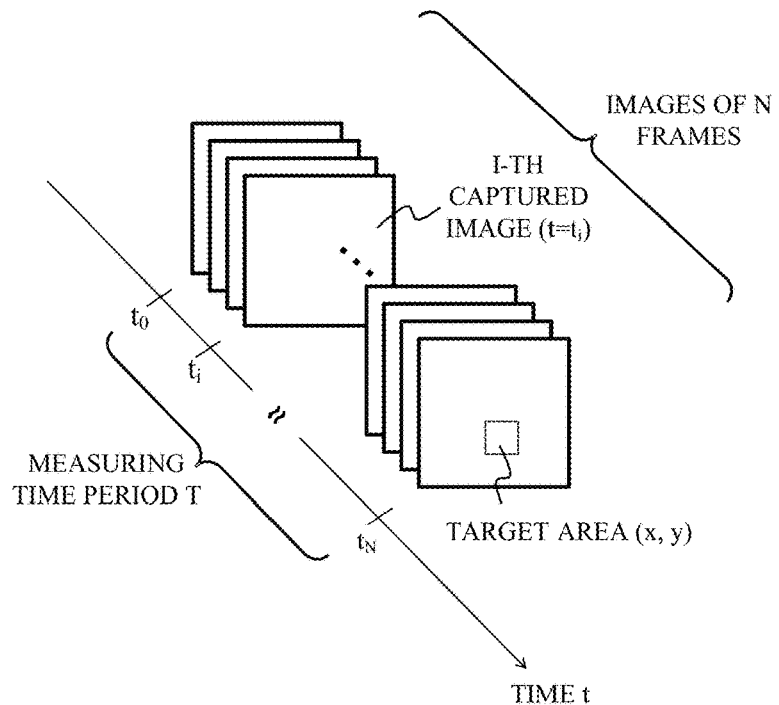
FIG. 7 is a schematic view explaining measured signals according to a second embodiment.

First, a description will be given of the data acquisition in S2050 and data evaluation in S2060, with reference to FIG. 7. FIG. 7 is a schematic time-sequential view of images of N frames captured by the CCD 520 in a measurement period T ($=t_N-t_0$). Each image is captured at certain time $t=t_i$. These N images captured in the measurement time period T contains information regarding temporal variation of the blood vessel 410 in the test object 400. Herein, it is assumed that the whole imaging area does not change while these images are captured. In S2050, the N images are captured at a high speed, such as 1 to 100 ms. Next, in S2060, the N images are evaluated with respect to the previously set the target area in the captured image (for example, in S1000 or S2010). In S2060, the processing unit 600b calculates an objective function within the set target area in the captured image. This target area is set so as to contain the blood vessel 410. The data is evaluated by statistical process on each pixel in the target area of the N image frames. For example, the speckle contrast $C_t$ is calculated among the frames as follows by addressing a certain pixel (x, y) in the target area.

$$C_t(x,y)=\sigma_t(x,y)/<I(x,y)> \quad (2)$$

where $\sigma_t(x, y)$ and $<I(x, y)>$ are standard deviation and average intensity between captured frames in the pixel (x, y), respectively.

The measurement unit 500 can thus acquire a change of the optical property with time in the test object by performing a plurality of measurements within the measurement time. The thus calculated speckle contrast $C_t$ is a value that reflects the influence of the blood flow in the blood vessel 410 in the test object 400, similar to the first embodiment. For example, when the speckle contrast $C_t$ is compared between the pixels within the blood vessel 410 and the pixels of other steady area in the captured image, the former speckle contrast $C_t$ is smaller than the latter one. As an example, one data evaluating method in S2060 is to extract the blood vessel site in the target area from the image, and to monitor the speckle contrast $C_t$ of one arbitrary pixel in the target area as the objective function. Alternatively, a sum ($\Sigma C_t(x, y)$) or an average ($<C_t(x, y)>$) of the speckle contrasts $C_t$ of a plurality of pixels in the blood vessel area may be monitored. In addition, the speckle contrasts $C_t$ may be evaluated at a plurality of different positions in the blood vessel area, and a linear sum of them with arbitrary coefficients may be monitored. In any of aforementioned case, the speckle contrast $C_t$ is set as the objective function for the wavefront shaping process, and executes the wavefront shaping process so as to decrease the objective function.

According to the measurement of the first embodiment, the captured image contains the blood vessel 410 but the wavefront shaping process S2000 does not expressly specify the blood vessel site 410. On the other hand, this embodiment specifies the blood vessel site 410 in the image and evaluates the speckle contrast at the site. When the test object 400 contains a plurality of blood vessels, it is more effective to specify the blood vessels in order to shape the wavefront and take images as explained in this embodiment.

The wavefront shaping process S2000 according to this embodiment sets, in S2010, a pixel (x, y) or an area in the captured image as the target area to be evaluated in S2060. At this point, the blood vessel 410 may be extracted by the image processing and the specified pixels may be evaluated as the target area. Alternatively, pixels containing the blood vessel 410 and its surrounding pixels may be set as the target area. The objective function may be based on the speckle contrast $C_t$ as expressed in Expression (2). The incident wavefront is shaped by iterating the data acquisition in S2050 and the data evaluation in S2060, as described above, with respect to the objective function. The process after the wavefront shaping may be executed based on FIG. 2 as described in the first embodiment.

The light irradiation in S3000 in FIG. 2 uses the wavefront obtained in S2000, as described above, and the image is obtained in S4000 by scanning the incident angle over the target area in the test object 400. In scanning, for example, the SLM 320 may be placed on a multi-axis stage and the stage may be sequentially tilted according to the scanning amount of the SLM 320. Alternatively, a linear phase shift corresponding to the scanning may be added to the phase distribution obtained in S2000 and set onto the SLM 320. Thus, the controller 600c may control the SLM 320 so as to scan the test object 400 with the wavefront-shaped light. This scan is performed within a so called memory effect range where correlation of scattering is preserved. Even when the incident angle is changed, the focusing effect on the blood vessel 410 obtained in S2000 is maintained because scattering is correlated. This effect can also provide an image near the blood vessel 410 (within the range of the memory effect). The range of the memory effect may be obtained in advance by calculating a correlation between the images obtained with different incident angles.

The light irradiation in S3000 may increase the light intensity output from the light source unit 200 if necessary, and take images of the test object 400.

The data acquisition in S2050 may set an image size to be as small as possible, in order to increase the frame rate of the CCD 520, as long as the blood vessel 410 is within the image.

Furthermore, as disclosed in Rong Liu, Jia Qin, and Ruikang K. Wang, "Motion-contrast laser speckle imaging of microcirculation within tissue beds in vivo," Journal of Biomedical Optics, Vol. 8(6)060508 (2013) (simply referred as "Liu" hereinafter), this embodiment may use a method for calculating a difference between each frame of the N images, and calculating a standard deviation where the background is removed or suppressed. The method disclosed in Liu may be used so as to precisely extract the blood vessel 410 from the test object 400. A standard deviation calculated after such processing is performed may be used as the objective function.

Third Embodiment

Figure 8:
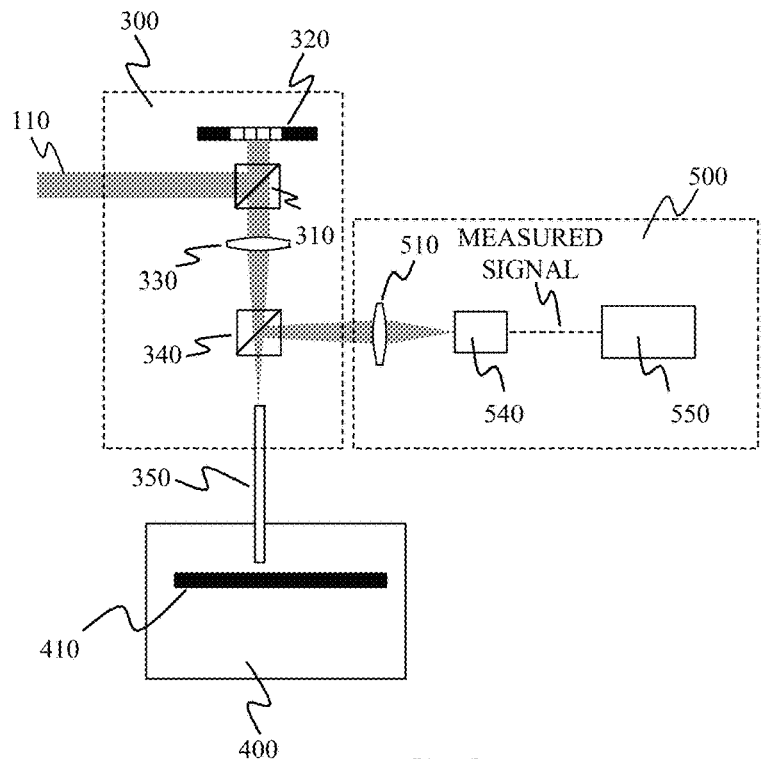
FIG. 8 is a schematic view of part of an apparatus according to a third embodiment.

A description will now be given of an imaging method and an imaging apparatus according to a third embodiment of the present invention. The apparatus according to this embodiment also has a basic configuration illustrated in FIG. 3. However, a characteristic configuration of the wavefront shaping and light irradiating unit 300 and the measurement unit 500 in this embodiment, will be described with reference to FIG. 8 that is an illustrative drawing.

A wavefront of the light 110 output from the light source unit 200 is shaped by the SLM 320, and the light is coupled with an optical fiber 350 via the optical system 330. The test object 400 (containing the blood vessel 410) is irradiated by the light emitted from the exit end of the optical fiber 350. The optical fiber 350 may be a fiber bundle of single-mode fibers or one multi-mode fiber.

Part of light that has entered and scattered in the test object 400 passes through the blood vessel 410, is backscattered and is input to the optical fiber 350 as light to be detected. This detected light is reflected on the BS 340 and enters the measurement unit 500. The measurement unit 500 includes an optical system 510 for focusing the light output from the unit 300 on a photodetector 540, the photodetector 540, and a correlator 550 configured to measure a temporal correlation of the signal from the photodetector 540 in real time. The photodetector 540 may be a single detector, such as a photodiode (PD), or an avalanche photo-diode (APD), or a photomultiplier (PMT). The signal from the photodetector 540 may be amplified by an amplifier. The photodetector 540 can be an area sensor, however, a single detector may be desirable because of faster response and higher sensitivity. The correlator 550 also performs A/D-conversion of the signal from the photodetector 540, and calculates and outputs the correlation of the obtained digital signal.

The imaging apparatus according to the present invention is applicable to an endoscope that inserts the optical fiber 350 into the test object 400 to observe inside of the test object. The basic imaging flow in this apparatus is similar to that of illustrated in FIG. 2. A description will now be given of the characteristic wavefront shaping process according to this embodiment.

First, a description will be given of a temporal autocorrelation signal measured in this embodiment. The photodetector 540 detects light that has entered the test object 400 and passed through the blood vessel 410. When the autocorrelation is calculated between time $t=0$ and $t=\tau$ among signals measured in the measurement time period from $t=0$ to $\tau$, the correlation $G_1(\tau)$ of the electric field expressed below is measured.

$$G_1(\tau) = \langle E(0)E^*(\tau)\rangle \qquad (3)$$

The correlation output from the correlator 550 is not a correlation of the electric field E, but a correlation $G_2(\tau)$ of the light intensity I as follows.

$$G_2(\tau) = \langle I(0)I^*(\tau)\rangle \qquad (4)$$

There is a following relationship between $G_1(\tau)$ and $G_2(\tau)$, and a correlation of $G_1(\tau)$ is indirectly measured.

$$G_2(\tau) = \langle I\rangle^2 + \gamma |G_1(\tau)|^2 \qquad (5)$$

where $\gamma$ is a parameter depending on the measurement condition.

Figure 9:
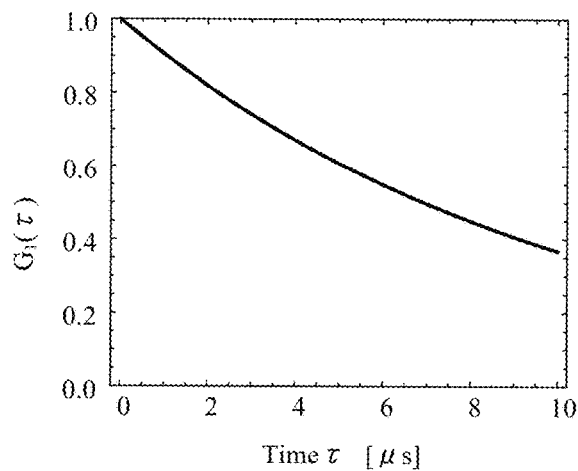
FIG. 9 is a schematic view for explaining a measured signal according to the third embodiment.

A signal of the correlation $G_1(\tau)$ attenuates with time in accordance with a change of scattering caused by the blood flow, as schematically illustrated in FIG. 9. This temporal correlation is the statistical value obtained through statistically processing a plurality of measured signals. The temporal change of the correlation $G_1(\tau)$ attenuates significantly as the blood flow increases (as the change increases). In addition, as an amount of detected light passing through the changing site, such as a blood vessel, relatively increases, the correlation $G_1(\tau)$ also significantly attenuates. Therefore, a value of the correlation $G_1(\tau)$ can be used as a monitoring signal. For example, when the wavefront is shaped so that $G_1(\tau)$ can significantly attenuate, an amount of the detected light that passes through the blood vessel site relatively increases. Herein, $G_1(\tau)$ may be properly normalized as in $G_1(\tau) = \langle E(0)E^*(\tau)\rangle / \langle |E(0)|^2\rangle$. A description will now be given of wavefront shaping process using the correlation $G_1(\tau)$ according to this embodiment.

The basic flow of the wavefront shaping process is similar to that of illustrated in FIG. 4. First, the objective function is set based on a correlation value output from the correlator 550 in S2010. For example, the process calculates a magnitude of the attenuation of the correlation $G_1(\tau)$ in a certain measurement time period $\tau$, such as $\tau=5$ μs for example. The magnitude of the attenuation may be a value of $G_1(\tau)$ after the time period $\tau$ as compared to $G_1(0)=1$, or an average change rate ($=<|\partial G_1(\tau)/\partial \tau|>$) of $G_1(\tau)$ in the measurement time period. The magnitude of the attenuation of the correlation value output from the correlator 550 is set as the objective function. In S2050, the correlation value is acquired through the detection by the detector 540 during the measurement time period $\tau$ and output from the correlator 550. In S2060, the attenuation is evaluated with respect to the measured correlation value. The subsequent process flow is similar to that of in the first embodiment. In S2080 the phase is selected so that the objective function $G_1(\tau)$ or a reciprocal of $|\partial G_1(\tau)/\partial \tau|$ can become small. The wavefront shaping process S2000 enables the generation of an incident light to be efficiently focused on the blood vessel 410 in the test object 400.

The optical property, such as an absorption property and a scattering property, in the blood vessel site may be measured with the above wavefront in S3000 and S4000 illustrated in FIG. 2, and a spectral property may be measured by changing the wavelength of the incident light. Thus, the local optical property in the certain target area may be measured.

Figure 10:
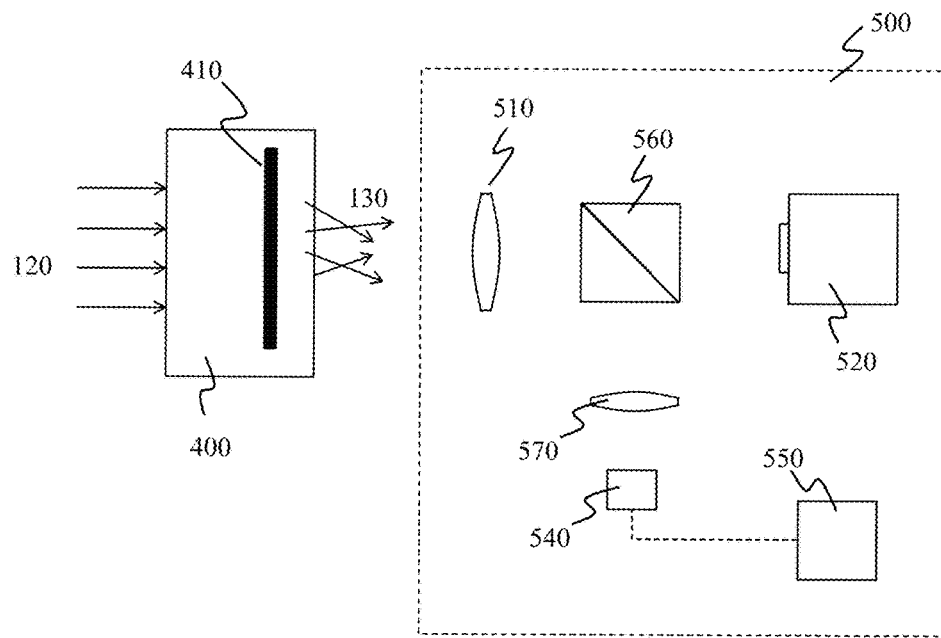
FIG. 10 is a schematic view of part of another apparatus according to the third embodiment.

Another apparatus according to this embodiment schematically illustrated in FIG. 10 combines a measurement of the correlation $G_1(\tau)$ and image captured by the CCD in the measurement unit 500. The measurement unit 500 according to this embodiment may include an image capturing unit configured to capture the test object 400. The light emitted from the test object 400 enters the measurement unit 500, and part of it passes a BS 560 via an optical system 510 and is imaged on a CCD 520. Another part of the light is reflected on the BS 560, and detected by a PD 540 via an optical system 570. The signal output from the PD 540 is digitized, and the correlation function $G_1(\tau)$ is measured by a correlator 550. Herein, the signal detected by the PD 540 corresponds to part of the signal captured by the CCD 520.

Referring now to FIG. 4, a description will be given of the wavefront shaping process using the apparatus including the measurement unit 500, in particular, S2010, S2050 and S2060 that are characteristics of this embodiment. Initially, the target area that contains the blood vessel 410 to be measured is set based on the image captured by the CCD 520 as the objective function setting in S2010. The optical system 570 and the PD 540 are adjusted so that the PD 540 can detect the signal from the area corresponding to the blood vessel 410. The area used to measure the correlation $G_1(\tau)$ may be adjusted by confirming the previously measured image. Thus, this apparatus can specify the target area first and then measure the correlation $G_1(\tau)$. As described above, the objective function is set as a reciprocal of the magnitude of the attenuation of the correlation $G_1(\tau)$ in a certain measurement time period $\tau$. Alternatively, at the same time, the image is captured by the CCD 520, and the speckle contrast $C_s$ (or $C_t$) may be evaluated and added to the objective function. The objective function may be evaluated so that both the speckle contrast and the reciprocal of the attenuation of the correlation $G_1(\tau)$ can be small. Alternatively, the value of the speckle contrast $C_s$ in an area may be set as a constraint condition, and keep the speckle contrast $C_s$ within a range of the constraint condition, and the objective function may be evaluated so that $G_1(\tau)$ can more significantly attenuate.

From S2050 to S2060, the objective function is evaluated based on the outputs from the CCD 520 and the correlator 550. Finally, in S2080, a phase distribution that minimizes the objective function is selected for each pattern, and the wavefront is shaped.

Fourth Embodiment

A description will now be given of an imaging method and an imaging apparatus according to a fourth embodiment of the present invention. The imaging apparatus according to this embodiment has the same configuration according to the first embodiment illustrated in FIG. 3 or may have the configuration according to the third embodiment illustrated in FIG. 10.

This embodiment evaluates a contrast of a signal from the blood vessel site in the captured image in addition to the speckle contrast or the correlation as the objective function evaluated in wavefront shaping process S2000.

Figures 11A, 11B:
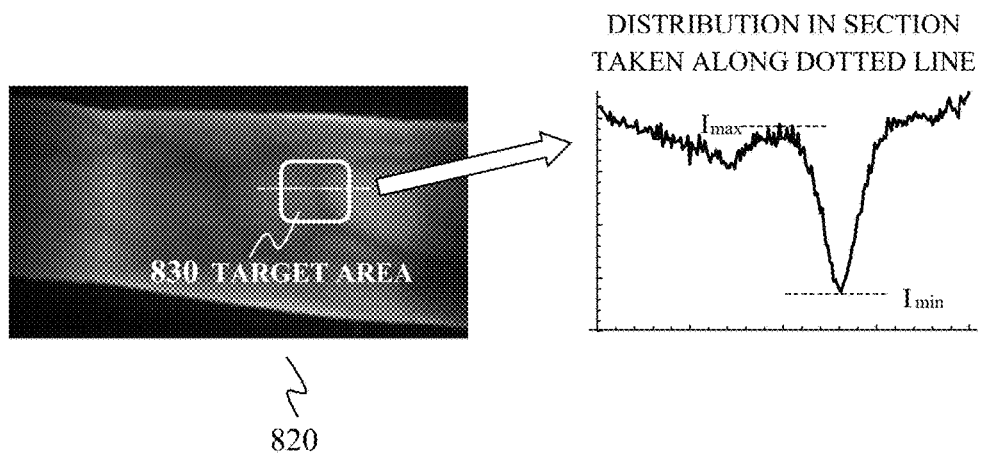
FIGS. 11A and 11B are schematic views of part of an apparatus according to a fourth embodiment.

As schematically illustrated in FIGS. 11A and 11B, a target area 830 is set in the image 820 captured in the CCD 520 (FIG. 11A). In this target area, a contrast value V of a signal, caused by the absorption of the blood vessel, is evaluated based on an arbitrary one-dimensional sectional distribution (FIG. 11B) which contains the blood vessel site.

$$V=(I_{max}-I_{min})/(I_{max}+I_{min}) \quad (6)$$

where $I_{max}$ and $I_{min}$ are a maximum value and a minimum value near the blood vessel site.

Typically, light does not reach deep enough at an absorptive object in the scattering medium, such as a living tissue, due to scattering. Therefore, in imaging, the contrast of the absorptive object decreases. On the other hand, when a larger amount of light is focused on an area near the blood vessel site, the signal contrast V improves. In order to improve the contrast V, the wavefront shaping process can be executed in addition to the speckle contrast.

In S2010, the objective function $\Phi$ is set as follows using the two parameters as variables and arbitrary weight coefficients $\alpha$ and $\beta$.

$$\Phi=\alpha C_s+\beta/V \quad (7)$$

The image is acquired in S2050, and the speckle contrast $C_s$ and the signal contrast V of the absorption image are measured based on the captured image, and the objective function is evaluated based on Expression (7) in S2060. More specifically, the processing unit 600b calculates the contrast value of the image obtained by the image capturing unit, such as the CCD 520 illustrated in FIGS. 3 and 10. In addition, the processing unit 600b calculates the objective function in accordance with Expression (7) using the contrast value and the speckle contrast $C_s$ (or the statistical value, such as the standard deviation and the average value of the light intensity I) as variables. In S2070 to S2071, this procedure is repeated by updating the phase, and the phase that minimizes the objective function $\Phi$ is read out and set as the phase of the pattern in S2080. The incident wavefront is shaped by iterating this procedure with different patterns. After the incident wavefront is obtained, the test object 400 is measured in accordance with the measurement flow illustrated in FIG. 2. Thereby, this embodiment shapes the wavefront so as to focus the light on the changing site caused by the blood flow, and directly controls the quality of the observed image through the wavefront shaping.

This embodiment combines the signal contrast V with the speckle contrast $C_s$ expressed in Expression (1), but may combine the signal contrast V with the speckle contrast $C_t$ expressed in Expression (2) or the correlation function $G_1(\tau)$ expressed in Expression (3).

As described above, the present invention utilizes an optical change in the test object. The present invention extracts this change by statistically processing the measurement data, shapes the wavefront of the light incident on the test object so that the change becomes remarkable by monitoring the obtained objective function, and then irradiates the light onto the test object. This embodiment is applicable to imaging, a variety of optical measurements, and diagnosis, by efficiently irradiating light onto a changing spot in the test object. The signal source is not limited to the blood vessel, as long as the dynamic optical property component can be measured in the test object. The test object is not limited to the biological tissues, such as a human body, and the present invention is applicable to any media that satisfy the above condition. The objective function may be generated by arbitrarily combining the evaluated values obtained by the described statistical processing.

The present invention can focus light inside the test object in a noninvasive and noncontact manner with a relatively simple apparatus configuration. In addition, the present invention is robust to unexpected noises by the difference, and can provide precise measurement or imaging of the optical property in the test object.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-102449, filed May 20, 2015, which is hereby incorporated by reference herein in its entirety.

What is claimed is:

1. A control apparatus comprising:
a data acquiring unit configured to acquire a measured signal obtained by measuring light emitted from a scattering test object onto which light is irradiated;
a processing unit configured to calculate an objective function that varies in accordance with a statistical value obtained by statistically processing the measured signal, wherein, in a case where the statistical value includes at least one of a standard deviation, a variance, or an average value of an intensity of the measured signal, the objective function is a speckle contrast based on the standard deviation, the variance, or the average value, and, in a case where the statistical value includes a temporal correlation of the measured signal, the objective function is set based on the temporal correlation; and
a controller configured to change a spatial modulation amount of a wavefront of the light irradiated onto the scattering test object so as to minimize the objective function, wherein the spatial modulation amount includes at least one of a phase modulation amount or an amplitude modulation amount.

2. The control apparatus according to claim 1, wherein the controller is configured to determine the spatial modulation amount when the objective function is minimum, and control the data acquiring unit and the processing unit to iteratively perform a processing by changing the spatial modulation amount.

3. The control apparatus according to claim 1, wherein the controller is configured to set a target area in the measured signal, and
wherein the processing unit is configured to calculate the objective function in the target area.

4. The control apparatus according to claim 3, wherein the scattering test object contains an area in which an optical property changes with time, and
wherein the controller is configured to set the area in which an optical property changes with time, to the target area.

5. The control apparatus according to claim 1, wherein the controller is configured to provide control so as to scan the scattering test object with the light having a modulated wavefront.

6. A measurement apparatus comprising:
a modulator configured to modulate a wavefront of light irradiated onto a scattering test object;
a measurement unit configured to measure light emitted from the scattering test object and to output a measured signal; and
a control apparatus configured to control the modulator and the measurement unit,
wherein the control apparatus includes:
a data acquiring unit configured to acquire the measured signal output from the measurement unit;
a processing unit configured to calculate an objective function that varies in accordance with a statistical value obtained by statistically processing the measured signal, wherein, in a case where the statistical value includes at least one of a standard deviation, a variance, or an average value of an intensity of the measured signal, the objective function is a speckle contrast based on the standard deviation, the variance, or the average value, and, in a case where the statistical value includes a temporal correlation of the measured signal, the objective function is set based on the temporal correlation; and a controller configured to change a spatial modulation amount of the modulator for the wavefront of the light irradiated onto the scattering test object so as to minimize the objective function, wherein the spatial modulation amount includes at least one of a phase modulation amount or an amplitude modulation amount.

7. The measurement apparatus according to claim 6, wherein the measurement unit includes an image capturing unit configured to capture an image of the test object, and
wherein the processing unit is configured to calculate a contrast value of the image obtained from the image capturing unit, and an objective function in which the contrast value and the contrast value are set as variables.

8. The measurement apparatus according to claim 7, wherein the objective function is larger when the contrast value has a first value than when the contrast value has a second value larger than the first value.

9. The measurement apparatus according to claim 6, wherein the scattering test object contains an area in which an optical property changes with time, and the measurement unit is configured to obtain a change of the optical property with time by spatially and temporally performing a plurality of measurements.

10. A control method comprising the steps of:
acquiring a measured signal obtained by measuring light emitted from a scattering test object onto which light is irradiated;
calculating an objective function that varies in accordance with a statistical value obtained by statistically processing the measured signal, wherein, in a case where the statistical value includes at least one of a standard deviation, a variance, or an average value of an intensity of the measured signal, the objective function is a speckle contrast based on the standard deviation, the variance, or the average value, and, in a case where the statistical value includes a temporal correlation of the measured signal, the objective function is set based on the temporal correlation; and
changing a spatial modulation amount of a wavefront of the light irradiated onto the scattering test object so as to minimize the objective function, wherein the spatial modulation amount includes at least one of a phase modulation amount or an amplitude modulation amount.

11. The control method according to claim 10, wherein the controlling step determines the spatial modulation amount when the objective function is minimum, and controls the acquiring step and the processing step to repetitively perform processing by changing the spatial modulation amount.

12. A non-transitory computer-readable storage medium for enabling a computer to execute a control method, wherein the control method includes the steps of:
acquiring a measured signal obtained by measuring light emitted from a scattering test object onto which light is irradiated;
calculating an objective function that varies in accordance with a statistical value obtained by statistically processing the measured signal, wherein, in a case where the statistical value includes at least one of a standard deviation, a variance, or an average value of an intensity of the measured signal, the objective function is a speckle contrast based on the standard deviation, the variance, or the average value, and, in a case where the statistical value includes a temporal correlation of the measured signal, the objective function is set based on the temporal correlation; and
changing a spatial modulation amount of a wavefront of the light irradiated onto the scattering test object so as to minimize the objective function, wherein the spatial modulation amount includes at least one of a phase modulation amount or an amplitude modulation amount.

* * * * *